United States Patent
Kanor

[11] 3,941,317
[45] Mar. 2, 1976

[54] METHOD AND APPARATUS FOR TISSUE DISAGGREGATION

[75] Inventor: Steven E. Kanor, Hastings-on-Hudson, N.Y.

[73] Assignee: LNIH, Inc., Hastings-on-Hudson, N.Y.

[22] Filed: Oct. 26, 1973

[21] Appl. No.: 410,050

[52] U.S. Cl. ...... 241/21; 23/259; 241/84;95;199.11
[51] Int. Cl.² ...................... B02C 19/08; B01L 3/00
[58] Field of Search ............... 241/1, 15, 21, 30, 84, 241/95, 199, 199.11; 23/259

[56] References Cited
UNITED STATES PATENTS

| | | | |
|---|---|---|---|
| 1,186,598 | 6/1915 | Mueser | 241/84 |
| 2,561,273 | 7/1951 | Hamilton | 23/259 X |
| 3,421,858 | 1/1969 | Quinn | 23/259 X |
| 3,458,139 | 7/1969 | Edebo | 241/1 |
| 3,556,414 | 1/1971 | Eberly | 241/1 |
| 3,560,162 | 2/1971 | Mittleman | 23/259 |
| 3,865,551 | 2/1975 | Saiki et al. | 241/199.11 |

OTHER PUBLICATIONS

Vaage, "A Mechanical Technique for Obtaining High Yields of Viable Dispersed Tumor Cells," Transplantion, Vol. 6, No. 1, Jan. 1968, pp. 137–139.

*Primary Examiner*—Roy Lake
*Assistant Examiner*—Craig R. Feinberg
*Attorney, Agent, or Firm*—Pennie & Edmonds

[57] ABSTRACT

A method of disaggregating tissue, particularly those containing relatively soft cells of body organs, to component cells, is disclosed as well as apparatus for carrying out the method which permits obtaining relatively large quantities of single cells or small groups of cells, the membrane and contents of which are structurally and chemically intact and not adversely affected by the disaggregation process.

14 Claims, 3 Drawing Figures

METHOD AND APPARATUS FOR TISSUE DISAGGREGATION

BACKGROUND OF THE INVENTION

In a wide variety of medical research and treatment techniques, notably those related to immunology and cell diseases, a preliminary requirement is the availability of relatively large quantities of functional cells, either singly or in small aggregates, which cells (parenchyma) have been separated from the stroma, i.e., the skeletal or connective cells which support them in the particular organ but which do not directly perform the function of that organ. The process of treating biological tissue so as to remove the stroma and separate out the parenchyma into individual cells with intact membranes is called disaggregation.

Disaggregation has been carried out by a variety of methods. One of them, homogenization, involves breaking up the tissue in a vessel by high-speed whirling blades. Grinding techniques have been employed wherein the tissue is ground between a pestle and a screen to break up the cells. Neither method provides a satisfactory yield of intact cells.

Perfusion is a technique wherein the natural blood vessel structure is employed to carry to the cells an agent which breaks down the adhering forces between cells and between cells and stroma. However, this changes the cell membranes beyond use.

Certain methods of disaggregation are described in a PhD Thesis of D. L. McCollester, entitled "Studies of the Isolation of Cell Membranes With Particular Reference to Skeletal Muscle", University of Cambridge, November, 1962. As outlined in the thesis, isolation of cell membranes first requires cell diaggregation, described as carried out initially on certain muscle tissue. Since the cell membrane in muscle tissue is about six times as thick as for other tissues, muscle can be disaggregated by homogenization without unduly destroying the membranes. However, the technique destroys too high a proportion of membrane of other parenchyma to permit obtaining useful quantities of cells.

Mortar and pestle-type apparatus has also been employed for cell disaggregation in which cells to be treated are placed on Nylon gauze within the mortar and rubbed and pressed vigorously between the pestle and the gauze (see Vaage, "A Mechanical Technique for Obtaining High Yields of Viable, Dispersed Tumor Cells", Transplantion, Vol. 6, No. 1 (January, 1968, pp. 137–39). However, the mechanical forces applied to the cells by this procedure tend to unduly damage the cell membranes, and the yield of intact cells is insufficient for certain purposes, e.g. those described in the McCollester Thesis, supra.

SUMMARY OF THE INVENTION

In accordance with the present invention, tissues are disaggregated substantially without damage to the structure or antigenic properties of their parenchymal cell walls in high yield by submerging them in a physiologic fluid medium not incompatible with the internal environment of the tissues in situ, between two biologically inert screen elements in substantial contact with one another over their operative surfaces, and moving the screen elements relative to one another while pressing the tissues between them. Unlike the action of the hard, smooth surface of the mortar against the screen mesh as mentioned in Vaage, which results in unduly low yields of intact cells, the co-action of the screens is believed to treat the cell membranes more gently during disaggregation, resulting in significantly higher yields of intact cells.

The structural and/or antigenic properties of the cell membranes can be damaged by (1) undue turbulence, such as is produced in homogenization; (2) passage through an air-water interface; (3) the presence of certain heavy metal ions or other complexing macromolecules; (4) pH variations; or (5) undue heat. All of the foregoing are to be avoided in carrying out the method of the invention.

An air-water interface tends to denature cell membranes passing through it, and is avoided in accordance with the invention by completely submerging in the fluid medium the tissue as well as the operative portions of the screen elements acting on it. Exposure to heavy metals will denature the interior of the disaggregated cells so that the substances comprising the interior can no longer be extracted.

Preferably, the screen elements are made of a biologically inert, medically accepted plastic. Exemplary of such materials are Nylon, Teflon, Delrin, Kel-F (all trademarks of E. I. duPont deNemours & Co.), acrylics, polyethylene and polypropylene. Alternatively, the screen elements may be metal screens coated with silicone rubber or with others of the above mentioned materials.

DESCRIPTION OF THE INVENTION

Additional features of the invention will become clear from an examination of the accompanying drawings in which.

Figure 1:
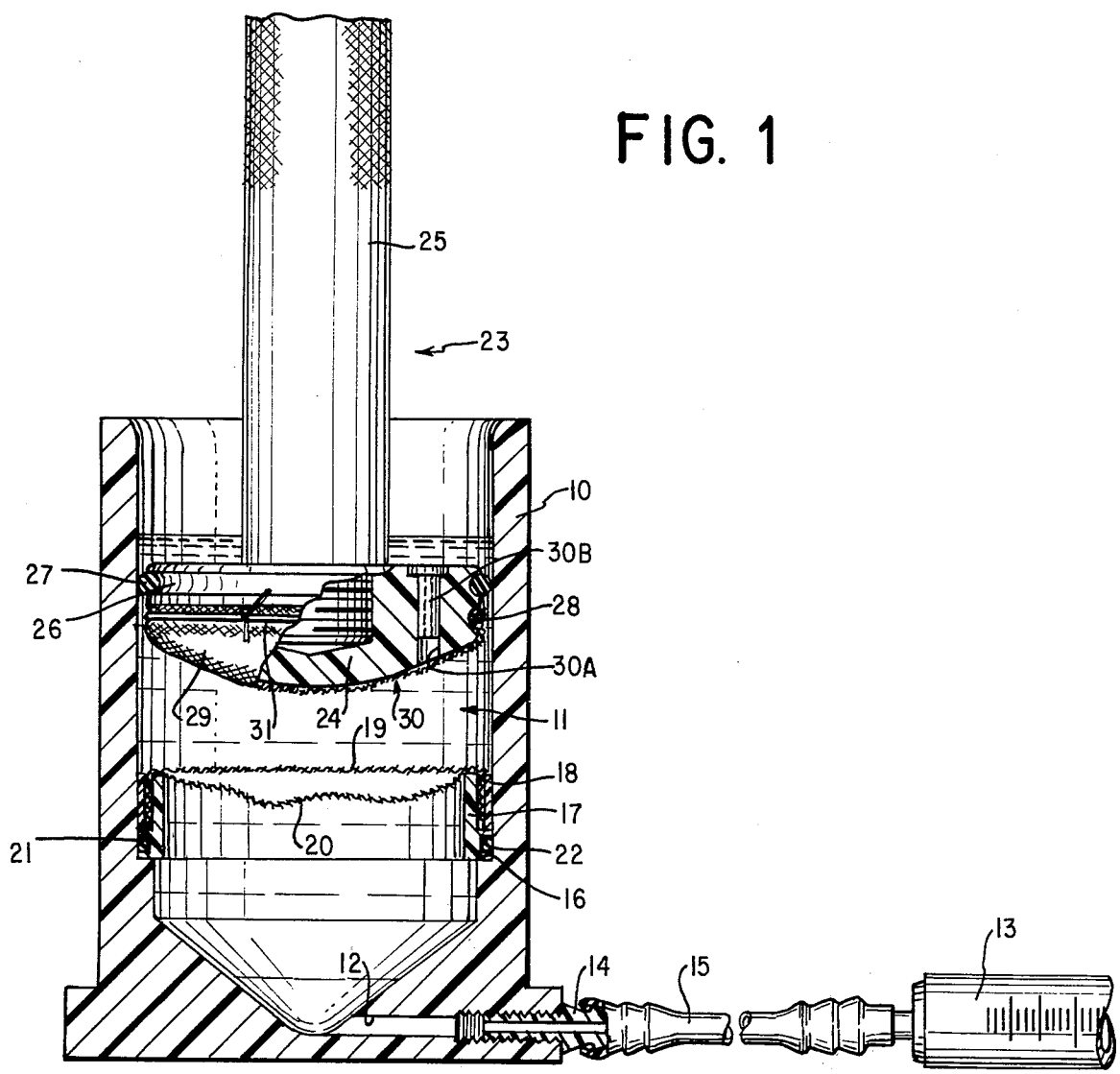
FIG. 1 is a side elevation view in partial section of a first embodiment of the invention.

The embodiment of the invention illustrated in FIG. 1 includes a cylindrically shaped mortar 10, open at the top and completely closed at the bottom. The mortar may be formed of acrylic or any other conveniently moldable material which is nontoxic (biologically inert) to the cells to be treated. It may also be formed of other materials which in themselves may be toxic providing the interior surface of the mortar is completely coated with a non-toxic substance, such as one of the plastics mentioned above, or silicone rubber.

The interior of the mortar, generally designated by numeral 11, openly communicates through a passage or tube 12 at the lower end of the mortar with a hypodermic syringe 13 or other variable volume element which presents to the fluid in it only biologically inert surfaces. As shown in FIG. 1, an exterior coupling 14 is provided which may be screwed into the base of the mortar and which couples at one end with passage 12 and at the other end with a flexible tube 15, the other end of which is coupled to the hypodermic syringe. This arrangement permits flushing fluid with the disaggregated cells from the mortar for collection in the hypodermic syringe.

The interior of the mortar 10 is provided with a step 16 upon which seals annular clamp 17. Annular clamp 17 is further provided with an annular closure element 18 dimensioned such that the space between the interior surface of the closure element and the exterior surface of the clamp is just enough to permit insertion of two screen elements 19 and 20 and to clamp both screen elements rigidly into position when assembled as shown. A biologically inert glue such as epoxy resin may be employed to fix the screens in place. A circumferential slot 21 in the lower exterior surface of clamp 17 is provided as an O-ring seat, in which O-ring 22 is placed to hold the entire clamp and closure ring along with screens 19 and 20 rigidly in place.

A pestle 23 is provided having a head 24 and a handle 25 which may conveniently be screwed together, as shown. The outer diameter of the head contains at its upper portion a circumferential groove 26 in which is provided an O-ring 27, the head 24, groove 26 and O-ring 27 being dimensioned such as to provide a substantially water-tight seal. Thus when the pestle 23 is moved up and down within the mortar it forces water or other fluid within the mortar outwardly through passage 12, and changes in volume are compensated by hypodermic syringe 13.

The lower portion of head 24 is provided with one or more grooves 28, and a layer of mesh 29 is placed over the surface 30 of the head and secured in place by a nylon cord 31 which fits in groove 28, or some other material capable of tightly fastening the mesh to the head.

Figure 2:
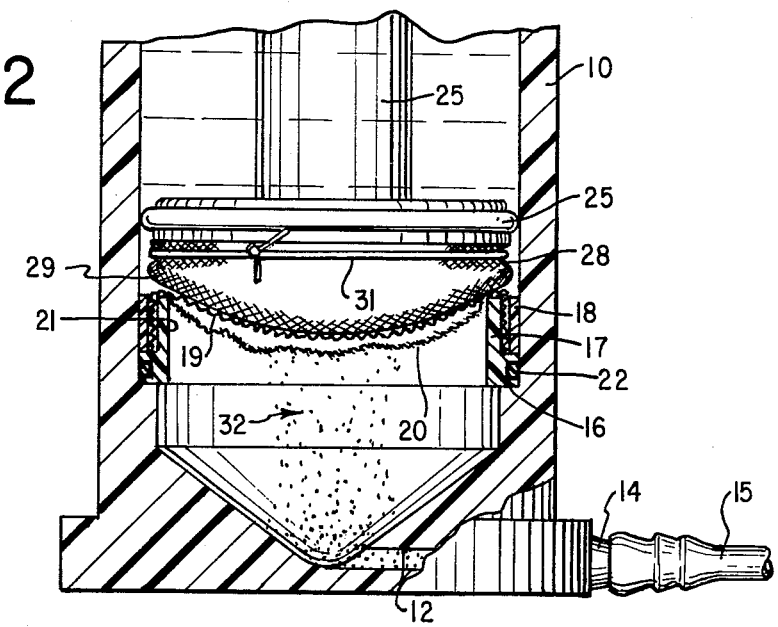
FIG. 2 is a side elevational view in partial section of the device of FIG. 1 showing the co-active screen elements engaged with each other.

The shape of the active surface 30 of head 24 should be such that when the mesh 29 covering it engages with mesh 19 provided on the mortar, as shown in FIG. 2, the two meshes readily contact one another over their entire active surfaces. To accomplish this, it has been found that the central portion of surface 30 should preferably have a radius of curvature roughly commensurate with the inside diameter of the mortar; for example, if the inside diameter of the mortar is 2½ inches, a radius of curvature of 2 to 2½ inches at the central portion of surface 30, with the outer portion of surface 30 tapering conically, as shown, provides good contact between the upper and lower screens as shown in FIG. 2.

The lower of the two screens which co-act to disaggregate the cells, i.e. screen 19, is stretched or placed between a clamp 17 and closure 18 such that its surface is essentially flat and is stretched to conform to the shape of head 30 when the screens 29 and 19 are engaged.

The lower or filter screen 20 is loosely inserted between clamp 17 and closure 18 so that it hangs out of contact with screen 19 even when the active screens 19 and 29 are in mesh, as shown in FIG. 2.

A tapped hole 30A and a screw closure 30B therefor are provided in the head 24 of the pestle to relieve any air bubbles trapped within the motar when the tissue to be disaggregated is placed between the screen elements.

It is essential in accordance with the invention that all materials and surfaces of the device which may come into contact with the fluid within the mortar be biologically inert. "Biologically inert" as used herein includes but is not limited to the requirement of freedom from metals, particularly ions of strontium and heavier metals, trivalent metals and other complexing macromolecules. Such metals and metal ions inhibit strongly later extraction of cell contents, a necessary step in ultimately recovering cell surface membranes and their associated antigens. Preferably, the entire mortar and pestle may be made of acrylic or an equivalent biologically inert medically acceptable plastic which is moldable. The active screen elements 29 and 19 and filter screen 20 may be similarly formed of Nylon or some other biologically inert, medically acceptable material as described above.

In operation, the pestle 25 is lifted out of the mortar and the latter is filled with a physiologic fluid medium which is not incompatible with the internal environment of the cells in situ, such as isotonic saline solution. The piston of hypodermic syringe 13 may be removed for this purpose permitting the fluid to fill passages 12, 14 and 15 and the syringe. The piston may then be inserted in the hypodermic syringe. The tissue to be disaggregated is then placed on screen 19 and the pestle inserted from the top until the active screen elements 19 and 29 mesh with one another as shown in FIG. 2. The piston of the hypodermic syringe may be removed for part of this operation or simply pulled out, depending on the respective volumes involved. The pestle is then rotated with respect to the mortar, maintaining downward pressure on the pestle so that the cells are disaggregated by the pressure and co-active rotational movements of screens 19 and 29. Typical downward pressures involved are on the order to 20 pounds.

The size of screens is generally indicated in terms of the size of the openings, specifically the length of one side of the square constituting the opening of the mesh. It is generally convenient to make both screens 19 and 29 the same size, although this is not necessary to the practice of the invention. Mesh size may vary generally as a function of the diameter of the cells being disaggregated, and should be at least twice and preferably at least a few times the cell diameter. The upper limit on mesh size is not critical, and disaggregation would take place even with meshes several orders of magnitude greater than the cell diameter. For example in disaggregating cells having diameters of 20 microns, disaggregation has been obtained in accordance with the invention using screens from 50 microns up to 3,000 microns in mesh size. Nevertheless, very large mesh sizes are more likely to pass relatively large aggregates of cells which then become trapped between screens 19 and 20 and either cannot be recovered or are not small enough to warrant recovery, so that smaller mesh sizes are preferred.

Filter screen 20 may be formed of the same material as the active screen elements and its mesh size should be roughly two times the diameter of the largest acceptable cell cluster, or group of cells. As an alternative to rotating the pestle, the pestle may be clamped stationary and the mortar rotated on a turntable. FIG. 2 shows small particles 32 of individual cells or groups of cells dropping down into the bottom of the mortar through the filter screen 20 as a result of disaggregation. Disaggregation may continue for only a few minutes or for longer times, and the optimum time may be determined by experience with the particular type of cell being disaggregated. The fluid in the unit may then be withdrawn by hypodermic syringe 13, by first lifting out or venting the pestle and withdrawing enough fluid to suck into the syringe cells and cell clusters which have dropped into the conical recepticle provided in the base of the mortar.

Figure 3:
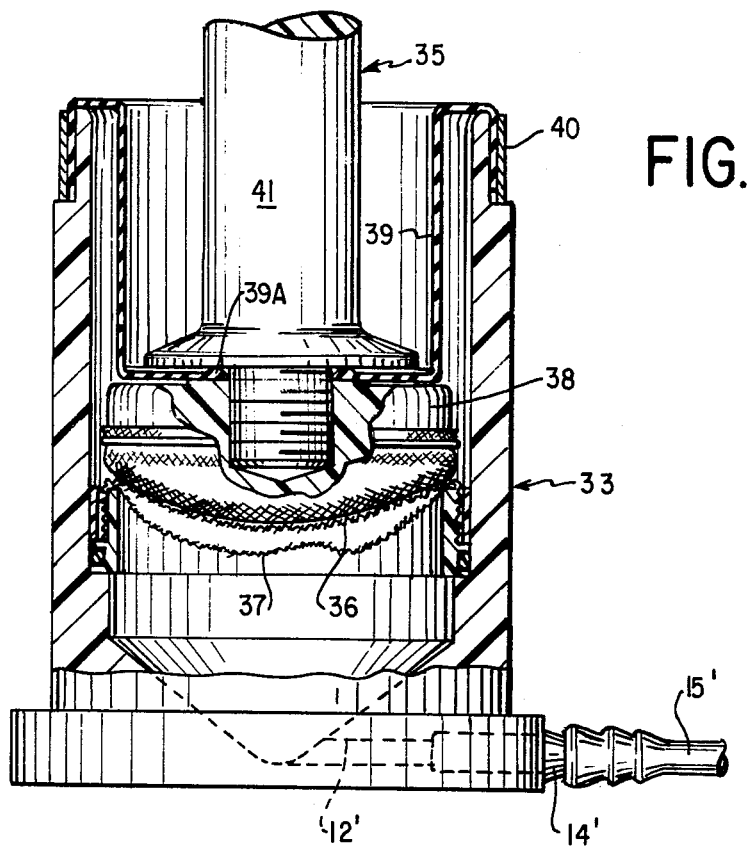
FIG. 3 is a side elevational view, in partial section of an alternative embodiment of the invention.

FIG. 3 illustrates an alternative embodiment of the invention in which the mortar 33 may be in all respects identical with mortar 10. The pestle 35 differs in certain respects, however, permitting oscillatory in addition to rotational movement between screen elements 36 and 37. In order to achieve this, the diameter of the pestle head 38 is made smaller than the inner diameter of the mortar in which it sits and a flexible rubber collar 39 is provided which extends from the upper surface of the head 38 about the upper rim of mortar 33 where it may be conveniently sealed by an annular ring 40. Flexible seal 39 permits a wide range of movement between the active screen elements 37 and 36 by both rotating handle 41 and by oscillating it from side to side. Collar 39 may include a thickened annular center portion 39A; the space between handle 41 and the top of pestle head 38 being limited by the screw fitting between them so that collar 39 is free to rotate with respect to the pestle, permitting free rotation between mortar and pestle.

In order to load cells into the device of FIG. 3, with pestle 35 removed from the mortar, the latter is filled with fluid and the pestle carefully inserted to minimize entrapment of air. If air bubbles are formed, they may be vented through the outlet line comprising passage 12' coupling 14', hose 15' and the hypodermic syringe (not shown) by turning the device upside down with the plunger of the syringe removed. The primed numbers in FIG. 3 indicate elements corresponding to the same numbers without primes in FIGS. 1 and 2. Collar 40 is then placed into position to seal the unit. The purpose of collar 39 is to maintain the device fluid tight while permitting oscillatory or rotating motion in place of the pure rotational motion preferably employed with respect to embodiments 1 and 2. Such motion is easily achieved by hand, the upper end of handle 41 describing a circle or rocking motion in a horizontal plane as well as rotation during disaggregation.

It has been found that the above described embodiments of the invention are particularly useful and convenient for carrying out the method of the invention to produce a high proportion of single cells or relatively small groups of cells which are undamaged by disaggregation and retain their structural, chemical and particularly their antigenic properties. It will be apparent to those skilled in the art that various changes may be made in the above described preferred embodiments of the invention without departing from the scope or spirit of the invention, which is defined solely in accordance with the following claims.

I claim:
1. A method of disaggregating cells without damaging the structure or antigenic properties of their cell membranes, comprising:
    submerging the cells to be disaggregated in a physiologic liquid between two screen elements, the surfaces of which are formed of biologically inert material free of metal ions poisonous to cell membranes and at least one of which permits passage of disaggregated cells through it to a volume of such physiologic liquid; and
    moving the screen elements relative to each other to disaggregate the cells for passage through said one screen element.
2. A method as defined in claim 1 wherein the screen elements have a mesh size greater than twice the diameter of the cells being disaggregated.
3. A method as defined in claim 2 wherein the mesh size of the screen elements is between about four times the diameter of the cells being disaggregated and about 2,000 microns.

4. Apparatus for disaggregating cells without substantially damaging the structure or antigenic properties of their cell membranes, comprising:
    a first screen element;
    means constituting a mortar for holding the first screen element and including a vessel within which the first screen element is disposed having its interior surface formed of a biologically inert material, said means being mounted in the vessel to hold said screen substantially in a horizontal plane in said vessel and including a filter screen element for passing only those disaggregated cells and clusters thereof that it is desired to accept;
    a second screen element;
    means in the form of a pestle for holding the second screen element and for moving it in contact with the first screen element such that the first and second screen elements are in mutual contact over substantially their entire surfaces, said pestle having a downwardly convex head about which the second screen element is mounted and including means for sealing the circumferential space between said head and the mortar to permit relative vertical movement between the mortar and the pestle;
    all of said screen elements having a surface formed of a biologically inert material and the first and second screen elements having mesh sizes at least twice the diameter of the cells to be disaggregated.
5. Apparatus as defined in claim 4 wherein said means for sealing the circumferential space between the pestle and the mortar is an O-ring mounted on the circumference of the head of the pestle permitting rotary motion between the mortar and pestle and hence between the first and second screen elements held respectively thereby to disaggregate cells placed between the first and second screen elements.
6. Apparatus as defined in claim 5 including means forming a passage extending from the bottom of the interior of the mortar and including a variable volume chamber for compensating changes in the volume of the mortar caused by movement therein of the pestle.
7. Apparatus as defined in claim 5 wherein said screen elements have a mesh size between about four times the diameter of the cells being disaggregated and about 2,000 microns.
8. Apparatus as defined in claim 4 wherein the means for sealing the circumferential space between the pestle and the mortar is a flexible member fastened to the head of the pestle and sealingly engaged about the top of the mortar to permit rocking and rotating the pestle with respect to the mortar to thereby disaggregate cells placed between said first and second screen elements.
9. Apparatus as defined in claim 8 including means forming a passage extending from the bottom of the interior of the mortar and including a variable volume chamber for compensating changes in the volume of the mortar caused by movement therein of the pestle.
10. Apparatus as defined in claim 4 wherein the interior surfaces of the mortar and pestle, the first and second screen elements and the filter screen are formed of a biologically inert plastic.
11. Apparatus as defined in claim 10 wherein the first and second screen elements are formed of flexible nylon mesh.
12. Apparatus for disaggregating cells substantially without damaging the structure or antigenic properties of their cell membranes, comprising:

a first screen element;
means for holding the first screen element;
a second flexible screen element;
means for holding the second screen element at its periphery and for moving it in contact with the first screen element such that the first and second screen elements are in mutual contact over substantially their entire surfaces;
said first and second screen elements having surfaces formed of a biologically inert material and having mesh sizes at least twice the diameter of the cells to be disaggregated.

13. Apparatus as defined in claim 12 wherein the means for holding the first screen element includes a vessel within which the first screen element is disposed, the interior surface of said vessel being formed of a biologically inert material.

14. Apparatus as defined in claim 13 wherein the means for holding the first screen element is mounted in the vessel to hold said screen element substantially in a horizontal plane therein, and including a filter screen disposed below the first screen element for passing only those disaggregated cells and clusters thereof which it is desired to accept, said filter screen element having surfaces formed of a biologically inert material.

* * * * *